United States Patent
Danger

(10) Patent No.: US 6,296,485 B1
(45) Date of Patent: Oct. 2, 2001

(54) FINISHER SET

(75) Inventor: Karl-Heinz Danger, Detmold (DE)

(73) Assignee: Gebruder Brasseler GmbH & Co. KG, Lemgo (DE)

( * ) Notice: Subject to any disclaimer, the term of this patent is extended or adjusted under 35 U.S.C. 154(b) by 0 days.

(21) Appl. No.: 09/546,812

(22) Filed: Apr. 11, 2000

(30) Foreign Application Priority Data

Apr. 12, 1999 (DE) ............................. 199 16 316

(51) Int. Cl.⁷ ................. A61C 3/02; A61C 3/06
(52) U.S. Cl. ............................. 433/165; 433/166
(58) Field of Search ..................... 433/165, 166

(56) References Cited

U.S. PATENT DOCUMENTS 2,109,086 * 2/1938 Coussement et al. ........... 433/166 X
2,902,763 * 8/1959 Heppe ............................ 433/165
4,389,192 * 6/1983 Neuwirth .......................... 433/166

FOREIGN PATENT DOCUMENTS

| GM 77 16 979 | 10/1977 | (DE). |
| 197 34 016 | 2/1999 | (DE). |

* cited by examiner

*Primary Examiner*—Nicholas D. Lucchesi
(74) *Attorney, Agent, or Firm*—Wolf, Greenfield & Sacks, P.C.

(57) ABSTRACT

The present invention relates to a finisher set for the cosmetic aesthetic treatment of teeth, the set comprising a plurality of finishers each including a shaft (b 5) adapted to be clamped into a drive means, as well as a conical head provided with cutting edges, characterized in that a first finisher (1) comprises a head (2) with helical cutting edges and a transverse cut, and that a second finisher (3) is provided with a head (4) having helical cutting edges.

16 Claims, 1 Drawing Sheet

FINISHER SET

FIELD OF THE INVENTION

The present invention relates to a finisher set for the cosmetic aesthetic treatment of teeth.

BACKGROUND OF THE INVENTION

The prior art already discloses finishers for the cosmetic aesthetic treatment of teeth; these finishers are offered as a set. Such a set comprises three finishers which are used one after the other. Each of said finishers comprises a conical head which is provided with straight cutting edges extending towards the tip. A finisher with eight cutting edges is used for prefinishing work, and in a subsequent working step the surface is treated with a second finisher having 16 cutting edges. To achieve a satisfactory and absolutely smooth surface, a finisher with 30 cutting edges is used in a subsequent third working step for obtaining an excellent, optically flawless surface with the help thereof.

When used as a set, the known finishers offer the possibility of generating high-quality surfaces, but have the drawback that the dentist needs three preparation instruments that must be used in successive order. In addition to the number of instruments needed, it is also necessary to change the same.

SUMMARY OF THE INVENTION

According to aspects of the present invention there is provided a finisher set which can be manufactured and used in an easy manner and at low costs and which reduces the number of instruments as well as the necessary treatment steps.

According to some aspects, the invention provides a finisher set which comprises a first finisher including a head with helical or twisted cutting edges and a transverse cut, as well as a second finisher including a head with helical cutting edges.

According to some embodiments of the invention, there is a finisher set for the cosmetic aesthetic treatment of teeth, comprising a plurality of finishers each comprising a shaft adapted to be clamped into a drive means, as well as a conical head provided with cutting edges, characterized in that a first finisher comprises a head with helical cutting edges and a transverse cut, and that a second finisher is provided with a head having helical cutting edges. The first finisher can have eight to sixteen cutting edges. Preferably, the first finisher has twelve cutting edges. The first finisher can include cutting edges having a helix angle of 5° to 15°. Preferably, the first finisher includes cutting edges having a helix angle of 10°. The second finisher can have sixteen to twenty-four cutting edges. Preferably, the second finisher has twenty cutting edges. The second finisher can have cutting edges having a helix angle of 20° to 30°. Preferably, the second finisher is provided with cutting edges having a helix angle of 25°. Finishers can be made from any dental compatible abrasive compound. Preferably, the finishers are made from cemented carbide.

BRIEF DESCRIPTION OF THE DRAWINGS

The invention shall now be described with reference to an embodiment taken in conjunction with the drawing, in which.

DETAILED DESCRIPTION

Figure 1:
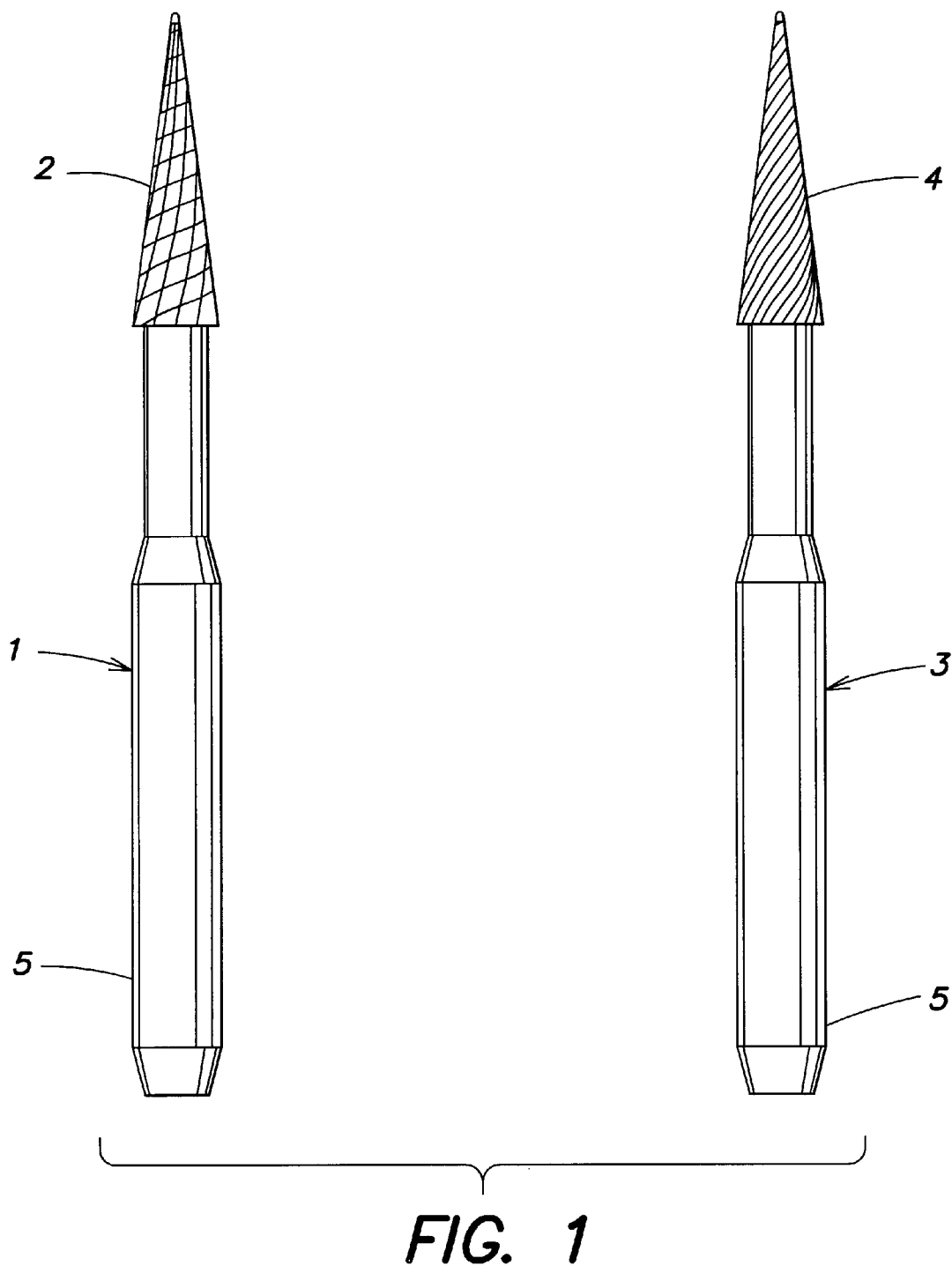
FIG. 1 shows the finisher set according to the invention.

The finisher set according to the invention is characterized by a number of considerable advantages. First of all, only two preparation instruments are needed for performing the finishing operation and for generating an absolutely smooth surface of a very high quality. The costs for the finisher set can thereby be reduced. Moreover, only two instruments have to be used, whereby the necessary set-up times during treatment are shortened. This has the effect that the entire treatment time can be reduced considerably as an instrument-changing operation is dispensed with.

The first finisher of the invention with slightly helical cutting edges and a transverse cut permits a considerably more efficient prefinishing operation than the prefinisher known from the prior art. With the help of the second finisher, which comprises a plurality of more strongly twisted or more helical cutting edges, a surface treatment of a particularly high quality becomes possible.

It has been found to be particularly advantageous when the first finisher is provided with twelve cutting edges. Furthermore, it is advantageous when it has a helix angle of the cutting edges of 10°. The second finisher is preferably provided with 20 cutting edges and has a helix angle of 25° in an advantageous development.

The finishers are preferably made from cemented carbide.

A first finisher 1 comprises a conical head 2 provided with cutting edges, as well as a shaft 5. Head 2 is provided with twelve cutting edges having a helix or twist angle of 10°. Furthermore, head 2 comprises a transverse cut or transverse toothing.

A second finisher 3 which also comprises a shaft 5 that can be clamped into a drive means is provided with a head 4 which comprises 20 cutting edges arranged at a helix angle of 25°.

The invention is not limited to the illustrated embodiment; rather many alterations and modifications are possible within the scope of the present invention. Therefore, the scope of the invention should be taken as the scope of the properly construed appended claims.

What is claimed is:

1. A finisher set for the cosmetic aesthetic treatment of teeth, comprising a plurality of finishers each comprising a shaft adapted to be clamped into a drive means, as well as a conical head provided with cutting edges, characterized in that a first finisher comprises a head with helical cutting edges and a transverse cut, and that a second finisher is provided with a head having helical cutting edges.

2. The finisher set according to claim 1, characterized in that said first finisher comprises eight to sixteen cutting edges.

3. The finisher set according to claim 2, characterized in that said first finisher comprises twelve cutting edges.

4. The finisher set according to claim 2, characterized in that said first finisher includes cutting edges having a helix angle of 5° to 15°.

5. The finisher set according to claim 4, characterized in that said first finisher includes cutting edges having a helix angle of 10°.

6. The finisher set according to claim 2, characterized in that said second finisher comprises sixteen to twenty-four cutting edges.

7. The finisher set according to claim 6, characterized in that said second finisher comprises twenty cutting edges.

8. The finisher set according to claim 2, characterized in that said second finisher is provided with cutting edges having a helix angle of 20° to 30°.

9. The finisher set according to claim 8, characterized in that said second finisher is provided with cutting edges having a helix angle of 25°.

10. The finisher set according to claim 1, characterized in that said first finisher includes cutting edges having a helix angle of 5° to 15°.

11. The finisher set according to claim 1, characterized in that said first finisher includes cutting edges having a helix angle of 10°.

12. The finisher set according to claim 1, characterized in that said second finisher comprises sixteen to twenty-four cutting edges.

13. The finisher set according to claim 12, characterized in that said second finisher comprises twenty cutting edges.

14. The finisher set according to claim 1, characterized in that said second finisher is provided with cutting edges having a helix angle of 20° to 30°.

15. The finisher set according to claim 14, characterized in that said second finisher is provided with cutting edges having a helix angle of 25°.

16. The finisher set according to claim 1, characterized in that said finishers are made from cemented carbide.

* * * * *